(12) United States Patent
Janda et al.

(10) Patent No.: US 9,669,433 B2
(45) Date of Patent: Jun. 6, 2017

(54) UNIVERSAL MINERAL SEPARATOR

(71) Applicant: JL ROBOTICS, INC., San Diego, CA (US)

(72) Inventors: Jeffrey J. Janda, San Diego, CA (US); Gavin A. D. Cutting, San Diego, CA (US)

(73) Assignee: JL Robotics Inc.

( * ) Notice: Subject to any disclaimer, the term of this patent is extended or adjusted under 35 U.S.C. 154(b) by 0 days.

(21) Appl. No.: 14/548,008

(22) Filed: Nov. 19, 2014

(65) Prior Publication Data
US 2016/0136694 A1     May 19, 2016

(51) Int. Cl.
| | | |
|---|---|---|
| *B07C 5/00* | (2006.01) | |
| *B07C 5/342* | (2006.01) | |
| *G01N 15/10* | (2006.01) | |
| *G01N 15/14* | (2006.01) | |
| *B07C 5/34* | (2006.01) | |

(52) U.S. Cl.
CPC ....... *B07C 5/3425* (2013.01); *G01N 15/1434* (2013.01); *G01N 15/1484* (2013.01); *B07C 5/34* (2013.01); *G01N 2015/1081* (2013.01); *G01N 2015/1087* (2013.01); *G01N 2015/149* (2013.01); *G01N 2015/1493* (2013.01)

(58) Field of Classification Search
CPC ......... B07C 5/34; B07C 5/3425; B07C 5/363; G01N 15/1404; G01N 15/1484; G01N 15/1434; G01N 2015/149; G01N 2015/1493; G01N 2015/1006; G01N 2015/1081; G01N 2015/1087; B01D 59/44; B01D 59/48; B07B 9/00

USPC ............................... 209/576, 639, 644, 44.2
See application file for complete search history.

(56) References Cited

U.S. PATENT DOCUMENTS

| | | |
|---|---|---|
| 5,030,279 A | 7/1991 | Krauth |
| 6,252,224 B1 | 6/2001 | Ohkawa |
| 6,258,216 B1 | 7/2001 | Ohkawa |
| 6,726,844 B2 | 4/2004 | Ohkawa et al. |

(Continued)

FOREIGN PATENT DOCUMENTS

AU     6506680 A     6/1981

OTHER PUBLICATIONS

PCT International Search Report, Application No. PCT/US2015/061138, Nov. 17, 2015.

*Primary Examiner* — Joseph C Rodriguez
*Assistant Examiner* — Kalyanavenkateshware Kumar
(74) *Attorney, Agent, or Firm* — Thomas VanZandt

(57) ABSTRACT

In accordance with the present invention, a pneumatic particle separator includes a base member formed with an elongated lumen. Also formed on the base member for fluid communication with the lumen are, in order, an air flow injection channel, the lumen, a diverter, and an n-number of type channels. Further, a particle injection channel is connected in fluid communication with the air flow injection channel. In this combination, when an air flow is established through the air flow injection channel and the lumen, particles are drawn by venturi action from the particle injection channel for single file transit through the lumen for analysis. A subsequent pneumatic diversion through the diverter then provides an exit for each particle from the base member through a preselected type channel for collection. The analysis performed in the lumen is used for an assay report.

13 Claims, 2 Drawing Sheets

(56) References Cited

U.S. PATENT DOCUMENTS

| | | |
|---|---|---|
| 6,956,217 B2 | 10/2005 | Ohkawa |
| 9,364,866 B2 * | 6/2016 | Davis .................... B07C 5/3425 |
| 2012/0276544 A1 | 11/2012 | Quake et al. |
| 2012/0298037 A1 | 11/2012 | Paul et al. |
| 2012/0298563 A1 | 11/2012 | Maynard et al. |
| 2013/0168301 A1 | 7/2013 | Dell'Endice et al. |

* cited by examiner

UNIVERSAL MINERAL SEPARATOR

FIELD OF THE INVENTION

The present invention pertains generally to geological assays, mineral processing, and particle analysis and sorting techniques. More particularly, the present invention pertains to field assay units that analyze samples containing powders or pre-crushed rock particles. The present invention is particularly, but not exclusively, useful as a field assay unit which pneumatically aligns all particles of the sample in single file during transport through the unit for an independent evaluation of each individual particle as to size and composition type.

BACKGROUND OF THE INVENTION

An assay involves the testing and examination of sample material to determine its composition and the quality of its ingredients. In the case of metals and ores it is sometimes necessary that the assay be done on site where the metal or the ore is located. In any event, the assay is preferably accomplished quickly, accurately and efficiently.

Heretofore, preparing an assay of an ore/mineral sample in real time has been quite labor intensive and has been limited by several operational considerations such as sampling and detection limitations. In general, it is first necessary to crush the ore/mineral into particles for bulk processing. Samples of the crushed material are then retrieved. Next, the samples are analyzed. As a practical matter, the specifics for a bulk analysis of samples are varied and can be quite different. For example, U.S. Pat. No. 8,151,632 for a "Method for defining element content and/or mineral content" discloses a mineral separation process in which a sample of crushed particles is bulk analyzed using a grain size analysis operation.

In the event, all ore/mineral assays have, as their primary objective, a determination of the mineral composition in the ore sample and its quality. The present invention, however, recognizes that a bulk analysis of ore/mineral samples for this purpose can be cumbersome, destructive and expensive. Further, the present invention recognizes that an analysis of an ore/mineral sample on a particle-by-particle basis provides for more precise measurements and more accurate results.

With the above in mind, it is an object of the present invention to provide a device and method for separating particles according to their composition, wherein each individual particle in a sample is individually evaluated and categorized, on a particle-by-particle basis, for an assay of the particles. Another object of the present invention is to provide a device and method for separating particles according to their composition, which pneumatically transports and separates the particles during processing. Yet another object of the present invention is to provide a device for separating particles according to their composition which is easy to manufacture, is simple to use and is comparatively cost effective.

SUMMARY OF THE INVENTION

In accordance with the present invention, a device for separating particles according to their composition (i.e. a particle separator) includes a base member which includes various embedded channels. Specifically, the channels are provided for moving particles through the base member. They include: an elongated central lumen, an air flow injection channel, a particle injection channel, a diverter, and a plurality of particle recovery channels. As envisioned for the present invention, the various channels are connected in fluid communication with each other so that pre-crushed particles can be pneumatically driven through the channels of the base member. Structurally, all of the channels have a characteristic dimension $d_L$ that is less than two hundred fifty microns ($d_L < 250$ µm). In the case of a circular cross-section, $d_L$ is a diameter; and in the case of a rectangular shaped channel, $d_L$ is a minimum distance between opposed sides.

For purposes of the present invention, the base member is a substantially flat, rectangular-shaped structure, and it is made of a transparent material, such as plastic, quartz, borosilicate or sapphire. The elongated lumen, noted above, is formed in the central portion of the base member and it has a first end and a second end. The air flow injection channel, also noted above, is formed in the base member to extend from the periphery of the base member for a connection in fluid communication with the first end of the lumen. Preferably, the air flow injection channel is coaxially oriented with the lumen and, importantly, the air flow channel is formed with a junction point.

Also formed into the base member is a particle injection channel which extends from the periphery of the base member for fluid communication with the junction point of the air flow injection channel. Additionally, a diverter is formed in the base member for fluid communication with the second end of the lumen. And further, an n-number of particle recovery channels are formed into the base member for respectively establishing fluid communication from the diverter to the periphery of the base member.

In an operation of the present invention, an air compressor is engaged with the air flow channel to create a flow of air through the air flow injection channel and into the central lumen. This air flow continues through the central lumen in the base member at an over-pressure $p_o$ that is greater than ambient pressure (e.g. 15 psig). A consequence here is that the flow of air through the air flow injection channel is accelerated to establish a venturi pump at the junction point.

A burst generator for creating bursts of particles is connected in fluid communication with the particle injection channel. The particle injection channel also interconnects the burst generator with the junction point on the air flow injection channel. Consequently, bursts of particles are sequentially drawn from the burst generator and through the particle injection channel by the venturi pump at the junction point, for further pneumatic transit through the central lumen. Importantly, in this operation, particles from the particle injection channel are aligned for single file transit through the central lumen for subsequent analysis. To assist with this alignment, the particle injection channel can be formed with a microfluidic serpentine section. As envisioned for the present invention, each particle passing through the channels of the base member will have a unique diameter $d_p$, where $d_p$ is less than $d_L$ ($d_p < d_L$).

Apart from the base member, the present invention includes an analyzer that is positioned with the base member for monitoring the central lumen of the base member. Its purpose is to determine a size, and a composition, for each particle as the particle transits through the central lumen. Structurally, the analyzer includes: a microcontroller, a camera, and a reflective spectrophotometer.

The camera of the analyzer is connected to the microcontroller for imaging each particle before it enters the lumen of the base member. Specifically, the image of the particle is used by the microcontroller to calculate a size for the particle, which is based on $d_p$. The reflective spectrophotometer, which is also connected to the microcontroller, is used for identifying the composition of each particle. In more detail, the reflective spectrophotometer includes a broadband light source for producing a light beam that is directed along a first beam path toward the lumen in the base member. It also has a grating for receiving a return light beam which is caused by a reflection of the light beam from a particle in the lumen. In this instance, the return light beam is directed toward the grating along a second beam path to create a spectrum. A line image sensor is also provided for capturing the spectrum of the return light beam for use by the microcontroller in determining the composition of the particle. In this combination, the first beam path for the light beam is at an angle α relative to the second beam path of the return light beam, where α is less than 90°. Thus, in its operation, the microcontroller analyzes the size of each particle together with the composition type of the same particle.

After the particles have been analyzed by the microcontroller, a sorter is provided to pneumatically separate the particles according to their composition. In detail, the sorter includes an n-number of gate valves that are mounted on the base member. Further, each gate valve is connected in fluid communication with a respective particle recovery channel. Thus, each gate valve is interconnected in fluid communication with the diverter.

An n-number of collection bins are individually connected with a respective particle recovery channel for receiving all particles having a predetermined same composition. To do this, depending on the particle composition, the microcontroller simultaneously opens one gate valve and closes the remaining (n−1) gate valves. This action then selectively directs particles of the same composition toward the open gate valve and into its associated collection bin. An assay of the particles can then be made.

For another embodiment of the present invention, it is to be appreciated that a plurality of devices can be simultaneously employed in combination. The objective here for using a combined plurality of devices is, of course, to increase the system throughput. In particular, the present invention envisions that a large number of devices can be operationally integrated to process as much as one ton of material (i.e. particles) in an hour.

In another aspect of the present invention, it is to be appreciated that by using a device of the present invention, a relatively minute trace of a target mineral can be detected in a very large sample of material (particles). Importantly, the detection of such a small amount of the target material may well justify additional assays.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
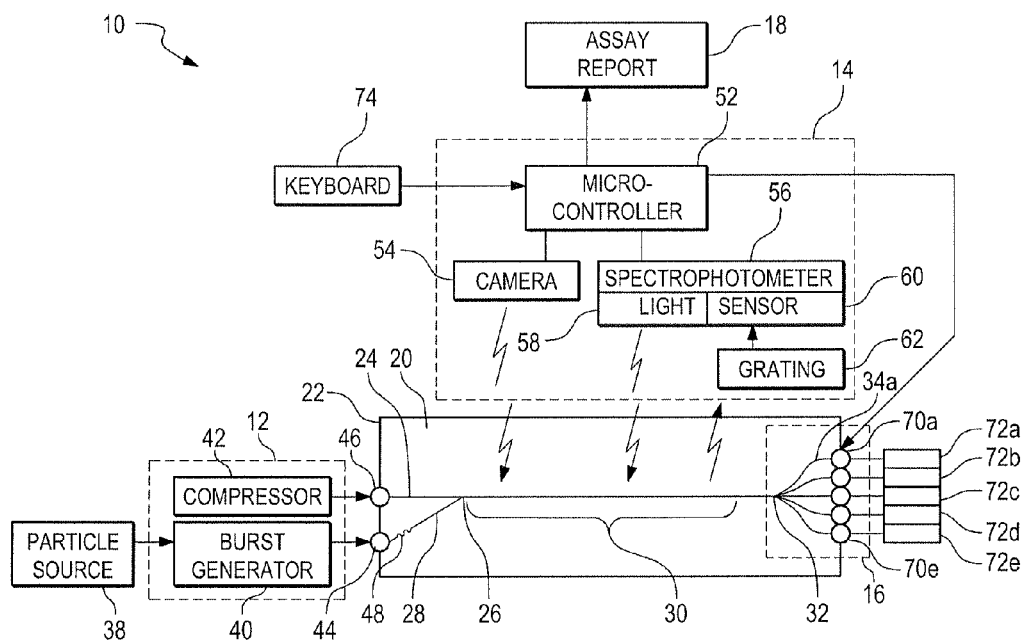
FIG. 1 is a schematic presentation of the operational components of a device for separating particles in accordance with the present invention.

A system for sorting particles and preparing an assay in accordance with the present invention is shown in FIG. 1 and is generally designated 10. As shown, the system 10 includes an injector unit 12, an analyzer 14, and a sorter 16. For purposes of the present invention, these components cooperate to process and analyze an ore/mineral sample for the preparation of an assay report 18 on the sample.

Structurally, an essential component of the system 10 is its base member 20. This base member 20 is preferably made of a transparent material, such as quartz, glass, borosilicate, sapphire or a clear plastic, and it is bounded by a periphery 22. Importantly, various channels are embedded in the base member 20 to establish fluid communication paths through the base member 20.

Figure 2:
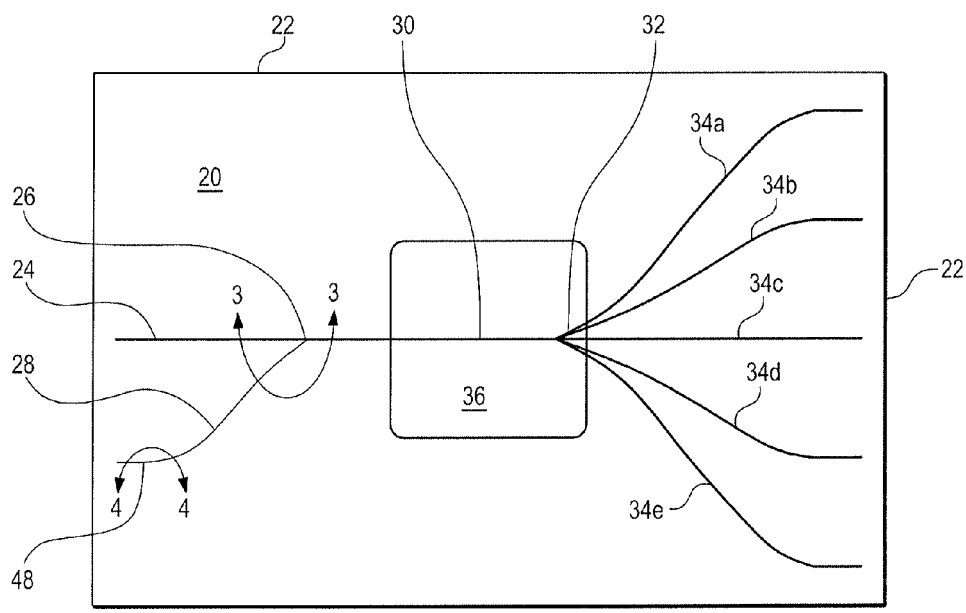
FIG. 2 is a top plan view of the base member of the present invention showing various particle channels connected in fluid communication with each other.

Referring to FIG. 2, it will be seen that the base member 20 is formed with an air flow injection channel 24 that extends from the periphery 22 to a venturi pump 26. As shown, the venturi pump 26 is also formed in the base member 20. Similar to the air flow injection channel 24, a particle injection channel 28 also extends from the periphery 22 to the venturi pump 26. An elongated central lumen 30 then extends from the venturi pump 26 to a diverter 32. At the diverter 32, the central lumen 30 divides into an n-number of particle recovery channels 34, of which the recovery channels 34a-e are exemplary. As shown, the central lumen 30 is coaxially aligned with the air flow injection channel 24, and the various particle recovery channels 34a-e extend from the diverter 32 to the periphery 22 of the base member 20. A window 36 is formed into the base member 20 over the central lumen 30. Functionally, the window 36 is an area of the base member 20 which has a diminished thickness to facilitate optical access to the central lumen 30.

As envisioned for the present invention, the air flow injection channel 24, the central lumen 30 and the recovery channels 34a-e will all have a characteristic dimension $d_L$. In general, $d_L$ will be less than around two hundred fifty microns ($d_L$<250 μm). On the other hand, the particle injection channel 28 has a characteristic dimension $d_{Lp}$, where $d_{Lp}$ will be less than about 150 microns ($d_{Lp}$<150 μm). Further, the cross-section of each channel 24, 28 and 34, and central lumen 30, may be either circular or rectangular. In the case of a circular cross-section, $d_L$ will be the diameter of the channel. In the case of a rectangular cross-section, $d_L$ will be a minimum distance between opposed sides of the channel.

Returning to FIG. 1, it will be seen that the system 10 includes a particle source 38, such as a hopper, for feeding pre-crushed particles of a sample ore/mineral into the system 10. As shown, the particle source 38 is connected to the burst generator 40 of the injector unit 12. It will also be seen that the injector unit 12 of system 10 includes an air compressor 42. For the system 10, the burst generator 40 is connected to the particle injection channel 28 by a solenoid valve 44, and the compressor 42 is connected to the air flow injection channel 24 by a solenoid valve 46. Further, both FIG. 1 and FIG. 2 show that near the solenoid valve 44, at the periphery 22 of the base member 20, the particle injection channel 28 is formed with a microfluidic serpentine section 48.

Figure 3:
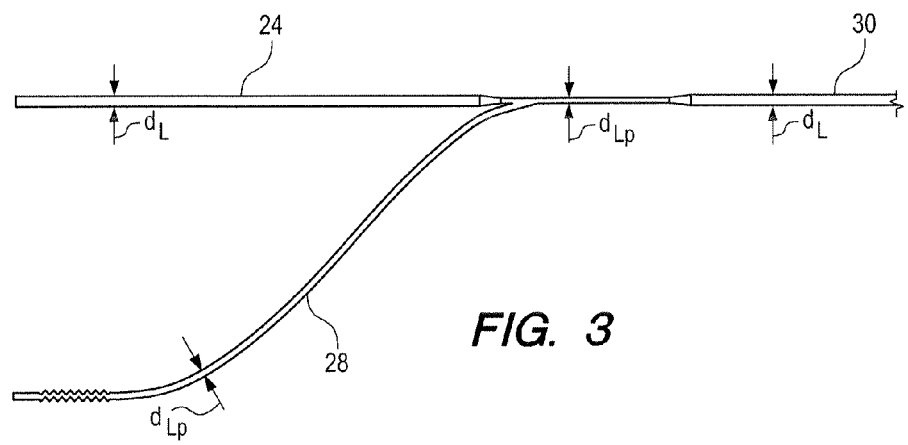
FIG. 3 is a view of the venturi pump established for the present invention, as shown by the line 3-3 in FIG. 2.

In detail, the venturi pump 26 is shown in FIG. 3 to effectively draw particles 50 from the particle injection channel 28 into the central lumen 30 of the base member 20. As is well known in the pertinent art, this pneumatic function is a result caused by pressure differentials in a fluid flow. Specifically, in the case of the present invention, the compressor 42 creates an over-pressure, $p_o$, in the air flow injection channel 24 that causes accelerated air to flow from the air flow injection channel 24 into the central lumen 30. As this air flow passes through the venturi pump 26, its higher velocity relative to air in the particle injection channel 28 causes a relatively lower pressure in the air flow injection channel 24. This pressure differential then draws particles 50 from the particle injection channel 28 into the venturi pump 26 for further transport through the central lumen 30. As shown in FIG. 3, the particle injection channel 28 approaches the air flow injection channel 24 at an angle of approximately 45 degrees. The particle injection channel 28 is connected in fluid communication to the air flow injection channel 24 at the venturi pump 26 at an angle of approximately 20 degrees.

Still referring to FIG. 3, for a detailed consideration of the venturi pump 26, it will be seen that various channels in the base member 20 have different characteristic dimensions. In particular, FIG. 3 shows that the air flow injection channel 24, and the central lumen 30, both have a substantially same diameter, $d_L$. On the other hand, the particle injection channel 28 and the venturi pump 26 at the juncture between the air flow injection channel 24 and the venturi pump 26 each have a diminished diameter $d_{Lp}$. Specifically, $d_{Lp}$ is approximately 150 μm and is less than $d_L$ which is approximately 250 μm ($d_L > d_{Lp}$). The consequence here is that the velocity of air entering the venturi pump 26 from the air flow injection channel 24 is increased because $d_L > d_{Lp}$. A further consequence of this is that the pressure differential in the venturi pump 26 is also increased because of the air velocity increase in the venturi pump 26.

In the action described above for the venturi pump 26, two factors are of particular importance. For one, the over-pressure $p_o$ generated by the compressor 42 needs to be above the ambient pressure. For the other, each particle 50 needs to have an effective diameter, $d_p$, which is less than the characteristic dimension $d_{Lp}$ disclosed above for the particle injection channel 28 ($d_p < d_{Lp}$). This latter requirement can be satisfied by incorporating an appropriate mesh screen with the particle source 38 that will reject particles 50 which exceed the pre-determined $d_p$.

Figure 4:
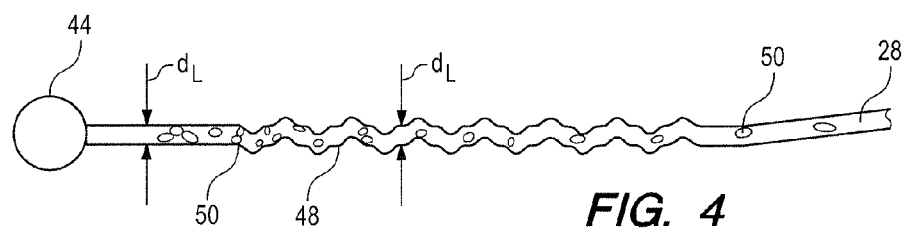
FIG. 4 is a view of the microfluidic serpentine established for the present invention, as shown by the line 4-4 in FIG. 2.

In FIG. 4 it is anticipated that as particles 50 enter the particle injection channel 28, from the burst generator 40 (not shown in FIG. 4) through the solenoid valve 44, it may happen they will do so in clumps. To help in separating the particles 50 from each other, a microfluidic serpentine section 48 can be formed into the particle injection channel 28. The intended consequence here is that the tortuous route which is created will cause collisions between the clumped particles 50 and walls of the microfluidic serpentine section 48. These collisions can then assist in separating the particles 50 from each other. This separation is important. As intended for the present invention, and best appreciated with reference to FIG. 3, an important aspect of the present invention is that all of the particles 50 are aligned in single file as they pass through the central lumen 30. As shown in FIG. 4, the microfluidic serpentine section 48 comprises multiple obtuse-angled bends in the particle injection channel 28 having a generally sinusoidal form and bumps on the segments between each bend of the particle injection channel 28.

Returning to FIG. 1 it will be seen that the analyzer 14 of the system 10 includes a microcontroller 52. Further, a camera 54 and a spectrophotometer 56 are connected directly with the microcontroller 52. Also, as shown in FIG. 1, the spectrophotometer 56 includes a light source 58, a sensor 60 and a grating 62. In their combined cooperation, the camera 54 and the spectrophotometer 56 are controlled by the microcontroller 52 to measure and analyze each individual particle 50 as it passes through the central lumen 30. In detail, the camera 54 will take a picture of each particle 50 that is then used by the microcontroller 52 to determine a size for the particle 50. Typically, this measurement of particle 50 will be accomplished before the particle 50 enters the central lumen 30. Then, after its size is determined, the spectrophotometer 56 is activated to determine a composition of the particle 50.

Figure 5:
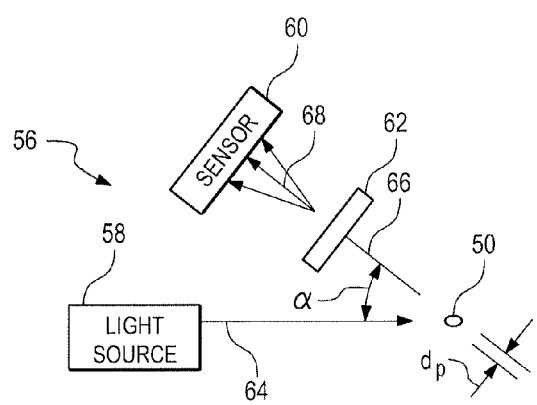
FIG. 5 is a schematic presentation of an operational configuration for components of the spectrophotometer of the present invention.

FIG. 5 shows the components of spectrophotometer 56 in a typical, operational configuration. As shown, it is to be appreciated that the particle 50 is transiting through the central lumen 30. During this transit, the light source 58 directs a beam of light along the beam path 64. Light that is reflected from the particle 50 will then return from the particle 50 along another beam path 66. The angle α between beam path 64 and beam path 66 will preferably be an acute angle in the range between 45° and 60°. Positioned on the beam path 66 is the grating 62 which is used to spread light reflected from the particle 50 into a spectrum 68. Then, using techniques well known in the pertinent art, the sensor 60 can analyze the spectrum 68 to determine the composition of the particle 50.

In FIG. 1, along with the diverter 32 and the particle recovery channels 34a-e, the sorter 16 is shown to include a plurality of solenoid valves 70a-e (only solenoids 70a and 70e are designated in FIG. 1). Nevertheless, as shown, each solenoid valve 70a-e is connected between a respective particle recovery channel 34a-e and a collection bin 72a-e. Further, for reasons set forth below, the solenoid valves 70a-e are each individually connected with the microcontroller 52 for their separate activation. For purposes of this disclosure, it is to be appreciated there can be an n-number of particle recovery channels 34 in the sorter 16, with a corresponding n-number of solenoid valves 70 and collection bins 72. The number 5 for "n" as used in this disclosure is merely exemplary. Moreover, it is to be appreciated that although the base member 20 may be formed with an n-number of particle recovery channels 34, not all of the channels 34 need to be used for preparing the assay report 18.

Prior to an operation of the system 10 of the present invention, a user/operator (not shown) will use a keyboard 74 for inputting desired operational parameters to the microcontroller 52. For example, it may happen that the user/operator is interested in ascertaining the content of gold (Au) in a given sample of an ore/mineral. Further, consider the user/operator wants the gold particles 50 to be collected in collection bin 72a, with all other particles 50 being sent to the collection bin 72e. In this example, the fact that gold (Au) is to be investigated, the selection of collection bin 72a for this collection, the operation of burst generator 40, and the over-pressure $p_o$ that is selected for compressor 42, are all typical inputs for microcontroller 52.

In an operation of the system 10, the compressor 42 is activated and the solenoid valve 46 is opened to admit compressed air at an over-pressure $p_o$ into the air flow injection channel 24. Burst generator 40 is also activated and the solenoid valve 44 is pulsed to allow predetermined bursts of pre-crushed particles 50 into the particle injection channel 28. The particles 50 are then drawn into alignment by the venturi pump 26 for transit through the central lumen 30 in single file. During transit of the particles 50 through the central lumen 30 they are sized using images taken by the camera 54, and their composition is determined by the spectrophotometer 56. After passing through the central lumen 30, each particle 50 is directed to a specific collection bin 72a-e, according to its composition. In the example given here, gold particles 50 are pneumatically directed by the diverter 32 into the collection bin 72a. Specifically, this pneumatic direction of gold particles 50 is accomplished by opening the solenoid valve 70a, while closing all of the other solenoid valves 70. On the other hand, the remaining particles 50 (i.e. non-gold) are pneumatically directed into the collection bin 72e by opening the solenoid valve 70e while the solenoid valves 70a-d are closed. It is envisioned for the present invention that the particles 50 may be native gold, native silver, acanthite, chalcopyrite, sphalerite, and rare earth minerals such as bastnasite, monazite and xenotime. As will be appreciated by the skilled artisan, this selective direction of particles 50 through the diverter 32 can be accomplished under computer-control, in accordance with input provided by the user/operator.

While the particular Universal Mineral Separator as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A pneumatic device for separating particles according to their composition which comprises:
    a source of pre-crushed particles, wherein each particle has a unique diameter $d_p$;
    a base member made of a transparent material and formed with an elongated lumen extending through the base member, wherein the lumen has a first end and a second end, with a cross-section having a characteristic dimension $d_L$ approximately 250 microns, and further wherein $d_p$ is less than $d_L$ ($d_p < d_L$), wherein, for a circular cross-section, $d_L$ is a diameter, and for a rectangular shaped channel, $d_L$ is a minimum distance between opposed sides;
    an injector unit, including a pneumatic venturi pump connected in fluid communication with the first end of the lumen in the base member for pneumatically injecting a plurality of separated particles for single file transit through the lumen, wherein the injector unit comprises:
        a compressor for creating an air flow through the lumen in the base member;
        an air flow injection channel formed into the base member to connect the compressor in fluid communication with the first end of the lumen in the base member, for pneumatically injecting the particles into the lumen through the first end thereof at an over-pressure $p_o$ greater than ambient pressure;
        a burst generator mounted on the base member and connected between the source of pre-crushed particles and the base member for creating bursts of particles;
        and a particle injection channel formed into the base member for connecting the burst generator in fluid communication with the air flow injection channel at a junction point, wherein the particle injection channel is connected to an airflow injection channel at an acute angle, and wherein the creation of air flow through the air flow injection channel by the compressor establishes the venturi pump at the junction point for sequentially drawing particles in the bursts from the burst generator, and through the particle injection channel for further pneumatic transit through the lumen;
    an analyzer positioned with the base member for monitoring the lumen of the base member to determine a size, and a composition for each particle, as the particle transits through the lumen; and
    a sorter connected in fluid communication with the second end of the lumen in the base member for pneumatically diverting each particle from the lumen and into a predetermined collection bin for separation of the particles according to the composition of the particle.

2. A device as recited in claim 1 wherein the particle injection channel includes a microfluidic serpentine section located between the particle burst generator and the junction point to align the particles in single file, the microfluidic serpentine section comprising multiple obtuse-angled bends in the particle injection channel and a segment between each bend, wherein each segment has at least one bump.

3. A device as recited in claim 1 wherein the analyzer comprises:
    a microcontroller; a camera connected to the microcontroller for imaging each particle before the particle enters the lumen of the base member, wherein the image of the particle is used by the microcontroller to calculate a size for the particle; and
    a reflective spectrophotometer connected to the microcontroller for identifying the composition of each particle, wherein the microcontroller analyzes the size of each particle together with the composition of the same particle to prepare an assay report.

4. A device as recited in claim 3 wherein the reflective spectrophotometer further comprises:
    a light source for producing a light beam directed along a first beam path toward the lumen in the base member;
    a grating for receiving a return light beam, wherein the return light beam is caused by a reflection of the light beam from a particle in the lumen, and wherein the return light beam is directed toward the grating along a second beam path for creating a spectra; and
    a line image sensor for capturing the spectra of the return light beam for use by the microcontroller in determining the composition for the particle.

5. A device as recited in claim 4 wherein the beam path for the light beam is at an angle $\alpha$ relative to the beam path of the return light beam, and wherein $\alpha$ is less than 90°.

6. A device as recited in claim 1 wherein the sorter comprises:
    a diverter formed into the base member at the second end of the lumen; an n-number of gate valves mounted on the base member; an n-number of particle recovery channels formed into the base member for interconnecting the diverter in fluid communication with a corresponding gate valve; and an n-number of collection bins, wherein each collection bin is individually connected with a particle recovery channel for receiving particles having a predetermined same composition type.

7. A device as recited in claim 6 wherein the microcontroller simultaneously opens one gate valve and closes the remaining (n−1) gate valves to selectively direct particles of the same composition type toward the open gate valve and into its associated collection bin.

8. A device as recited in claim 7 wherein the composition type is a mineral selected from the group consisting of native gold, native silver, acanthite, chalcopyrite, sphalerite, bastnasite, monazite and xenotime.

9. A device as recited in claim 1 wherein the particle source comprises:
a hopper for receiving the pre-crushed particles; and a mesh for receiving a sample of particles from the hopper to remove oversized particles from the sample for recycling when a particle has a diameter greater than $d_p$.

10. A device as recited in claim 1 wherein the particle injection channel has a characteristic dimension $d_{Lp}$, where $d_{Lp}$ is approximately 150 microns.

11. A method for using a pneumatic device to separate particles according to their composition which comprises the steps of:
pre-crushing a mineral sample into a plurality of individual particles, wherein each particle has a unique diameter $d_p$; injecting compressed air into a base member at an over-pressure $p_o$ greater than ambient pressure for moving air through an air flow channel and a lumen formed into the base member, wherein the lumen has a first end and a second end, with a cross-section having a characteristic dimension $d_L$ approximately 250 microns, wherein the air flow channel is connected in fluid communication with the first end of the lumen and further wherein $d_p$ is less than $d_L$ ($d_p < d_L$), wherein, for a circular cross-section, $d_L$ is a diameter, and for a rectangular shaped channel, $d_L$ is a minimum distance between opposed sides;
drawing the particles into a particle injection channel, wherein the particle injection channel is formed into the base member in fluid communication with the air flow injection channel at a junction point, the particle injection channel connected to an airflow injection channel at an acute angle, wherein the creation of air flow through the air flow injection channel by the compressor establishes a pneumatic venturi pump at the junction point for pneumatically drawing particles in single file through the particle injection channel for further pneumatic transit through the lumen, the particle injection channel having formed therein a microfluidic serpentine section comprising multiple obtuse-angled bends in the particle injection channel and a segment between each bend, wherein each segment has at least one bump;
imaging each particle with a camera before the particle enters the lumen of the base member, wherein the image of the particle is used by a microcontroller to calculate a size for the particle;
identifying the composition of each particle during a transition of the particle through the lumen, wherein particle identification is accomplished by the microcontroller using a reflective spectrophotometer connected to the microcontroller; and
pneumatically diverting individual particles by microcontroller control from the second end of the lumen through a selected one of an n-number of particle recovery channels and to a corresponding gate valve mounted on the base member, wherein the diversion is accomplished according to the composition type of the particle as determined during the identifying step, and wherein an n-number of respective collection bins are individually connected with a gate valve and a respective particle recovery channel for receiving particles having a predetermined same composition type.

12. A method as recited in claim 11 wherein the diverting step is accomplished by the microcontroller simultaneously opening one gate valve while closing the remaining (n−1) gate valves to selectively direct particles of the same composition type toward the open gate valve and into its associated collection bin.

13. A method as recited in claim 11 wherein the particle injection channel has a characteristic dimension $d_{Lp}$, where $d_{Lp}$ is approximately 150 microns.

* * * * *